United States Patent [19]

Zeck et al.

[11] Patent Number: 4,925,483
[45] Date of Patent: May 15, 1990

[54] TRIAZINONE SYNERGISTIC COMPOSITIONS

[75] Inventors: Walter M. Zeck, Vero Beach, Fla.; Joe Synek, Overland Park, Kans.

[73] Assignee: Mobay Corporation, Pittsburgh, Pa.

[21] Appl. No.: 596,323

[22] Filed: Apr. 3, 1984

[51] Int. Cl.$^5$ .......................................... A01N 43/707
[52] U.S. Cl. ........................................................ 71/93
[58] Field of Search ............................................. 71/93

[56] References Cited

U.S. PATENT DOCUMENTS 3,671,523  6/1972  Westphal et al. ........................ 71/93
4,457,774  7/1984  Eve et al. ................................ 71/93

Primary Examiner—Glennon H. Hollrah
Assistant Examiner—Eric J. Kraus
Attorney, Agent, or Firm—Joseph C. Gil; Lyndanne M. Whalen

[57] ABSTRACT

A selectively herbicidal composition of matter comprising a herbicidally effective amount of
(A) 4-amino-6-tert.-butyl-3-methylthio-1,2,4-triazin-5(4H)-one, and
(B) 4-amino-6-tert.-butyl-3-ethylthio-1,2,4-triazin-5-(4H)-one.

The composition is especially suited for selectively killing monocotyledon and dicotyledon weeds in the cultivation of cereals and leguminous plants.

12 Claims, 1 Drawing Sheet

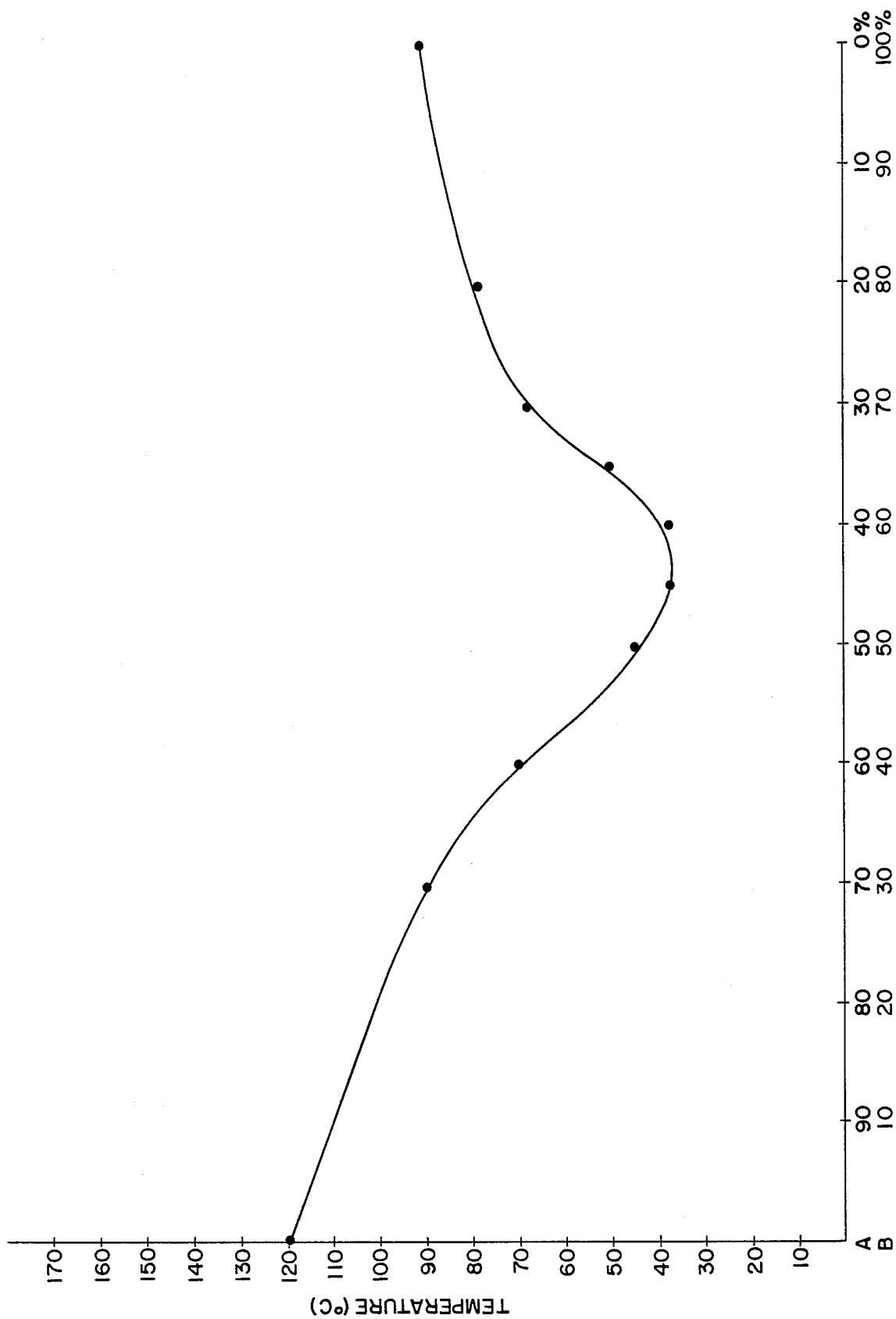

TRIAZINONE SYNERGISTIC COMPOSITIONS

The present invention relates to the use, in combination, of two known selective herbicides to obtain more than an additive effect with regard to undesired weeds.

4-Amino-6-tert.-butyl-3-methylthio-1,2,4-triazin-5-(4H)-one (A), common name metribuzin and available under the trademark Sencor, is disclosed in U.S. Pat. No. 3,671,523 and has found acceptance in practice for selectively combating weeds in soy beans, potatoes, tomatoes and alfalfa and, with severe limitations, in cereals. Its use in cereals is based exclusively on post-emergence treatment. It is not possible to use it in cereals by the pre-emergence method for tolerance reasons. In addition, for reasons of phytotoxicity toward the cereal, its use is recommended only with certain varieties of cereal, and even in this case only in a limited area.

The same patent discloses the 3-ethylthio homologue (B), viz. 4-amino-6-tert.-butyl-3-ethylthio-1,2,4-triazin-5-(4H)-one, whereas application Ser. No. 303,658, filed Sept. 18, 1981, now pending, discloses the use of (B) for selectively combating monocotyledon and dicotyledon weeds in cereal crops and leguminous crops before and after emergence of the plants. It also discloses (B) used in conjuction with specific other known herbicides.

It has now been surprisingly found that combinations of (A) and (B) exhibit greater weed conrol than the individual components, and that such combinations can be applied either before or after emergence of the desired crops and/or undesired weeds as well as being incorporated even before sowing.

In accordance with another feature of the invention, it has been found that the two ingredients interact so as to form a new physical form which remains liquid at temperatures much lower than where each individual component crystallizes.

Because of their synergy it was found that lower amounts can be employed for biological effectiveness thereby minimizing the risk of damage to the desired crop. Accordingly, the invention thus represents a great enrichment of selective herbicides especially in the cultivation of cereals and leguminosae.

Weeds, in the broadest sense, are to be understood as all plants which occur as undesirable in the growing of crops. Examples which may be mentioned of weeds which are destroyed by the combination to be used according to the invention and frequently occur in cereal crops and leguminous crops are:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Impmoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Monocotyledon weeds of the genera: Echinochloa, Sataria, Panicum, Digitaria, Phleum, Poa, Festuca, Eleusine, Brachiaria, Lolium, Bromu, Avena, Cyperus, Sorghum, Agropyron, Cynodon, Monocharia, Fimbristylis, Sagittaria, Eleocharis, Scirups, Paspalum, Ischaemum, Sphenoclea, Dactyloctenium, Agrostis, Alopecurus and Apera.

However, the use of the active combination according to the invention is in no way restricted to these genera, but also extends in the same manner to other plants.

The combination is particularly suitable for combating weeds in wheat and barley varieties of cereals and in the other crops such as peas, soybean and corn, the action being directed equally towards broad-leaved weeds (dicotyledoneae) and towards graminaceous weeds (monocotyledoneae), in particular *Avena fatua, Bromus, Alopecurus* and *Setaria*.

The weight ratios of the active compounds in the active compound combinations can vary within relatively wide limits. In general 0.01 to 1 part by weight of (A), preferably 0.05 to 0.5 part by weight, are present per part by weight of the triazinone (B).

The new combination can be converted to the customary formulations, such as solutions, emulsions, wettable powders, suspensions, powders, dusting agents, pastes, soluble powders, granules, suspension-emulsion concentrates, natural and synthetic materials impregnated with active compounds, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic materials, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, aryylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, can be used in the formulations.

It is possible to use colorants such as inorganic pigments, for example iron oxide, titanium oxide and Pressian Blue, and organic dyestuffs, such as alizarin dyestuffs and azo-metal phthalocyanine dyestuffs, and trace nutrients such as salts of iron, manganese, boron, copper, cobalt, molybdenum and zinc, as further additives in the formulations.

The formulations in general contain between 0.1 and 95 percent by weight of active compound combination, preferably between 0.5 and 90%.

The active compound combinations according to the invention are, in general, used in the form of finished formulations. However, the active compounds contained in the active compound combinations, can, also, be mixed in individual formulations when used, that is, to say, they can be used in the form of tank mixtures.

The new active compound combinations, as such or in the form of their formulations, can also be used as mixtures with other known herbicides for cereals and leguminosae, finished formulations or tank mixing again being possible. Mixtures with other known active compounds, such as fungicides, insecticides, acaricides, nematicides, bird repellents, growth factors, plant nutrients and agents which improve soil structure, are also possible.

The new active compound combinations can be used as such, in the form of their formulations or in the use forms prepared therefrom by further dilution, such as ready-to-use solutions, suspensions, emulsions, powders, pastes and granules. They are used in the customary manner of application, for example by watering, spraying, atomizing, dusting or scattering.

While the triazinone (A) can be applied to cereals only by the "post-emergence" method, and even then only with the further limitations mentioned, it is possible to apply the new active compound combinations to cereals both by the "post-emergence" method, by the "pre-emergence" method and also by incorporation into the soil before sowing.

The amount of active compound applied can vary within a substantial range, and depends, inter alia, on the weather and on soil factors. In general, the amounts applied are between 0.01 and 5 kg of active compound combinations per ha, preferably between 0.1 and 3 kg/ha.

The invention will be further described with reference to the accompanying drawing wherein the figure is a plot of crystallization or precipitation temperature vs. composition of a solution of (A) and (B).

The drawing shows a eutectic depression in melting point beginning with even as little as 1% of either ingredient, more pronounced with 20-80% of each, and most pronounced at about 40-60% of each.

The invention will be further described in the following examples wherein all parts are by weight unless otherwise expressed.

EXAMPLE 1

Mixtures were prepared containing various percentages by weight of active material (A) and (B). The compounds were mixed, melted and then permitted to cool slowly with stirring, while observing the temperature at which crystallization occurred. The relationship between temperature and composition is shown in the drwing. A minimum melting point of about 37° C. is shown at about 45/55 (A)/(B).

EXAMPLE 2

A small plot field trial was conducted using a $CO_2$-hand sprayer with T-jet 80015 nozzles delivering 235 liters per hectare of water. Plot size was 12 square meters with three replications. Soil type was a fine textured soil with 3-4% organic matter. The chemical was sprayed on the soil surface and incorporated down to 10 cm with a roto-tiller. After leveling off the plots the desired crop was seeded. Evaluations were thereafter made, as indicated, by determining the plant injury in percent. The results obtained are set forth in Table 1.

TABLE 1

| Active Ingredient | Kg/ha | % Control After 12 weeks | |
|---|---|---|---|
| | | Wild buckwheat | Cow Cockle |
| A | 0.125 | 30 | 20 |
| B | 0.5 | 57 | 40 |
| A + B | 0.125 + 0.5 | 97 | 86 |

EXAMPLE 3

The process of Example 2 was repeated in a soil containing about 10% organic matter. The results obtained were as follows:

TABLE 2

| Active Igredient | Kg/ha | After 11 weeks | | | |
|---|---|---|---|---|---|
| | | Hemp-nettle | % Control Chickweed | Wild buckwheat | % Injury of wheat |
| A | 0.25 | 3 | 10 | 20 | 0 |
| B | 1.25 | 0 | 0 | 0 | 0 |
| A + B | 0.125 + 1.25 | 30 | 5 | 50 | 0 |
| A | 0.25 | 3 | 10 | 20 | 0 |
| B | 1.5 | 0 | 0 | 13 | 0 |
| A + B | 0.125 + 1.5 | 50 | 15 | 73 | 0 |

EXAMPLE 4

The procedure of Example 2 was repeated with winter wheat with the following changes: the treatment was made after the emergence of crop and weeds by spraying some plots in the fall and others in the spring when plants were in the 2-3 leaf stage. For fall application, weed control was determined after 6 months and crop injury after 4 months. For spring application, weed control was determined 2 months later and crop injury 5 days later. The results obtained were as follows:

TABLE 3

| Active Ingredient | Kg/ha | Time of Appln. | % Control Cheatgrass | % Injury Wheat |
|---|---|---|---|---|
| A | 0.125 | Fall | 37 | 12 |
| B | 1.0 | Fall | 37 | 0 |
| A + B | 0.125 + 1.0 | Fall | 92 | 13 |
| A | 0.187 | Spring | 0 | 0 |
| B | 1.0 | Spring | 3 | 0 |
| A + B | 0.187 + 1.0 | Spring | 43 | 2 |
| A | 0.25 | Spring | 23 | 0 |
| B | 1.0 | Spring | 3 | 0 |
| A + B | 0.25 + 1.0 | Spring | 73 | 3 |

EXAMPLE 5

The process of Example 4 was repeated. The results obtained were as follows:

TABLE 4

| Active Ingredient | Kg/ha | Time of Appln. | % Control After 7 Weeks | | | % Injury Wheat |
|---|---|---|---|---|---|---|
| | | | Downy Brome | Field Pennycress | Tansy Mustard | |
| A | 0.28 | Spring | 16 | 33 | 41 | 0 |
| B | 1.0 | Spring | 16 | 34 | 15 | 0 |
| A + B | 0.28 + 1.0 | Spring | 75 | 99 | 95 | 5 |

EXAMPLE 6

The process of Example 4 was repeated. The results obtained were as follows:

TABLE 5

| Active Ingredient | Kg/ha | Time of Appln. | % Control After 7 Weeks | | | % Injury Wheat |
|---|---|---|---|---|---|---|
| | | | Downy Brome | Field Pennycress | Tansy Mustard | |
| A | 0.28 | Spring | 15 | 21 | 32 | 1 |
| B | 1.0 | Spring | 10 | 30 | 22 | 0 |
| A + B | 0.28 + 1.0 | Spring | 71 | 92 | 84 | 7 |

EXAMPLE 7

The process of Example 4 was repeated. The results obtained were as follows:

TABLE 6

| Active Ingredient | Kg/ha | Time of Appln. | % Control After 7 Weeks | | | % Injury Wheat |
|---|---|---|---|---|---|---|
| | | | Downy Brome | Field Pennycress | Tansy Mustard | |
| A | 0.28 | Spring | 18 | 45 | 37 | 0 |
| B | 1.0 | Spring | 15 | 30 | 41 | 0 |
| A + B | 0.28 + 1.0 | Spring | 61 | 97 | 92 | 5 |

EXAMPLE 8

A greenhouse trial was conducted as follows: treatments were made to sandy loam soil containing 2.5% organic matter in standard greenhouse flats 14×10 inches filled to a 3 inch depth, under a moving belt sprayer delivering 45 gallons per acre of spray solution through a T-jet flat fan nozzle of the type 8002. The treatments were made to the bare soil surface after seeding of crops and weeds. The trays were maintained under controlled temperature and watering regimens in the greenhouse for 3-4 weeks when evaluations were made for efficacy and plant injury by visual observations on a 0-100% scale. The results obtained were as follows:

TABLE 7

| Active Ingredient | Kg/ha | % Control | | | | % Injury | |
|---|---|---|---|---|---|---|---|
| | | Annual Morning Glory | Ivyleaf Morning Glory | Rape | Cheat | Wheat | Barley |
| A | 0.018 | — | — | 10 | — | 10 | 0 |
| B | 0.018 | — | — | 0 | — | 0 | 0 |
| A + B | 0.018 + 1.018 | — | — | 70 | — | 0 | 0 |
| A | 0.07 | 20 | — | — | — | 10 | 20 |
| B | 0.07 | 0 | — | — | — | 0 | 0 |
| A + B | 0.07 + 0.07 | 50 | — | — | — | 10 | 10 |
| A | 0.14 | — | — | — | 40 | 60 | 60 |
| B | 0.14 | — | — | — | 0 | 10 | 0 |
| A + B | 0.14 + 0.14 | — | — | — | 60 | 70 | 50 |
| A | 0.28 | — | 20 | — | 60 | 80 | 70 |
| B | 0.28 | — | 0 | — | 0 | 10 | 10 |
| A + B | 0.28 + 0.28 | — | 50 | — | 80 | 80 | 70 |

EXAMPLE 9

The process of Example 8 was repeated. The results obtained were as follows:

TABLE 8

| Active Ingredient | Kg/ha | % Control Cheatgrass |
|---|---|---|
| A | 0.0625 | 30 |
| B | 0.25 | 10 |
| A + B | 0.0625 + 0.25 | 60 |
| A | 0.0625 | 30 |
| B | 0.5 | 47 |
| A + B | 0.0625 + 0.5 | 98 |

It will be understood that the specification and examples are illustrative but not limitative of the present invention and that other embodiments within the spirit and scope of the invention will suggest themselves to those skilled in the art.

What is claimed is:

1. A selectively herbicidal composition of matter comprising a herbicidally effective amount of
   (A) 4-amino-6-tert.-butyl-3-methylthio-1,2,4-triazin-5(4H)-one, and
   (B) 4-amino-6-tert.-butyl-3-ethylthio-1,2,4-triazin-5(4H)-one, about 0.01 to 1 part by weight of (A) being present per part by weight of (B).
2. A composition according to claim 1, wherein about 0.05 to 0.5 part by weight of (A) is present per part by weight of (B).
3. A composition according to claim 1, wherein (A) and (B) are present in the form of mixed crystals containing about 1% to 99% by weight of each of them.
4. A composition according to claim 1, wherein (A) and (B) are present in the form of mixed crystals containing about 20% to 80% by weight of each of them.
5. A process for selectively killing monocotyledon and dicotyledon weeds in the cultivation of cereal and leguminous crops comprising applying to the crops or to a habitat thereof a selectively weed-herbicidally effective amount of a composition according to claim 1.
6. A process for selectively killing monocotyledon and dicotyledon weeds in the cultivation of cereal and leguminous crops comprising applying to the crops or to a habitat thereof a selectively weed-herbicidally effective amount of a composition according to claim 2.
7. A process for selectively killing monocotyledon and dicotyledon weeds in the cultivation of cereal and leguminous crops comprising applying to the crops or to a habitat thereof a selectively weed-herbicidally effective amount of a composition according to claim 3.
8. The method according to claim 5, wherein the composition is applied pre-emergence.
9. The method according to claim 4, wherein the composition is applied post-emergence.
10. The method according to claim 5, wherein the composition is applied prior to sowing of the crop.
11. A composition according to claim 1, comprising by weight about 40 to 60% of (A) and 60 to 40% of (B).
12. A composition according to claim 11, dissolved in a solvent.

* * * * *